United States Patent [19]
Gattuso

[11] Patent Number: 5,889,186
[45] Date of Patent: Mar. 30, 1999

[54] PROCESS FOR PREPARATION OF THE PHARMACEUTICALLY DESIRED (S)-OXETINE ENANTIOMERS

[75] Inventor: Mark J. Gattuso, Palatine, Ill.

[73] Assignee: UOP, Des Plaines, Ill.

[21] Appl. No.: 357,910

[22] Filed: Dec. 16, 1994

[51] Int. Cl.$^6$ .................................................. C07C 209/88
[52] U.S. Cl. ........................ 564/304; 564/302; 564/347
[58] Field of Search ...................................... 564/302, 304, 564/347

[56] References Cited

U.S. PATENT DOCUMENTS

| | | | |
|---|---|---|---|
| 2,985,589 | 5/1961 | Broughton et al. | 210/34 |
| 5,104,899 | 4/1992 | Young et al. | 514/646 |

OTHER PUBLICATIONS

Skrebnik, Ramachandran & Brown, *J. Org. Chem.*, 53, 2916, 1988.

Gao & Sharpless, *J. Org. Chem.*, 53, 4081, 1988.

E. J. Corey and G. A. Reichard, *Tetrahedron Letters,* 30, No. 39, 5207 (1989).

Schneider and Goergens, *Tetrahedron: Asymmetry,* No. 4, 525, 1992.

*Primary Examiner*—Richard L. Raymond
*Attorney, Agent, or Firm*—Thomas K. McBride; Eugene I. Snyder

[57] ABSTRACT

Improved processes for preparation of the (S)-oxetines in high enantiomeric purity centers on resolution using simulated moving bed chromatography of a racemic precursor early in the oxetine synthesis. Resolution is effected with high enantiomeric purity, and subsequent reactions of the desired enantiomer performed with high optical specificity to maintain enantiomeric purity. The undesired enantiomer may be racemized and recycled to the resolution phase to avoid undesired losses.

24 Claims, 3 Drawing Sheets

PROCESS FOR PREPARATION OF THE PHARMACEUTICALLY DESIRED (S)-OXETINE ENANTIOMERS

BACKGROUND OF THE INVENTION

At the molecular level biological systems are highly asymmetric; enzymes, proteins, polysaccharides, nucleic acids, and many other fundamental components of life are present in optically active form. The implications of this are profound; as a general proposition the interaction of a chiral molecule with an optically active site is a diastereomeric interaction, and the two enantiomers properly should be viewed as distinct compounds capable of acting in different ways. (R)-Asparagine has a bitter taste, whereas the (S)-isomer is sweet. It has been known for some time that for medicinals having at least one chiral center the pharmacological effectiveness of the enantiomers of the racemic mixture may differ substantially, and in some cases the pharmacological action itself may differ. An extreme example is provide by propranolol, where the major pharmacological effect of the (R)-isomer is as a contraceptive, whereas the major pharmacological effect of the (S)-isomer is as a beta-blocker.

Although the recognition of the desirability of using the pharmacologically and pharmaceutically more acceptable enantiomer is old, nonetheless the use of optically pure medicinals generally is relatively new, simply because of the difficulty and cost of resolution of the racemic mixture and/or the difficulty and cost of asymmetric synthesis of the desired enantiomer. The importance of stereochemical purity may be exemplified by (S)-propranolol, which is known to be 100 times more potent as a beta-blocker than its (R)-enantiomer. Furthermore, optical purity is important since certain isomers actually may be deleterious rather than simply inert. For example, the R-enantiomer of thalidomide was a safe and effective sedative when prescribed for the control of morning sickness during pregnancy. However, S-thalidomide was discovered to be a potent teratogen leaving in its wake a multitude of infants deformed at birth.

With recent chemical advances, especially in asymmetric synthesis, has come both an increase in the feasibility of selectively preparing the desired enantiomer of a given chiral medicinal, as well as increasing pressure on the pharmaceutical industry to make available only that enantiomer. An instructive example, pertinent to the subject matter of this invention, is the class of serotonin-uptake inhibitors represented by fluoxetine (whose racemate is available as Prozac™), tomoxetine, and nisoxetine, all of which have the structure (as the hydrochloride)

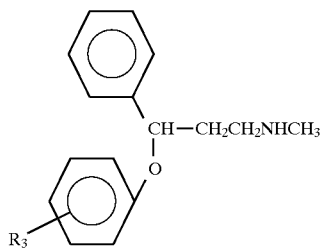

where $R_3$=4-$CF_3$, 2-$CH_3$, and 2-$C_2H_5O$, respectively.

Thus, Skrebnik, Ramachandran & Brown, *J. Org. Chem*, 53, 2916, 1988, used chirally modified boron compounds in the asymmetric reduction of prochiral ketones. From 3-chloropropiophenone there was prepared S-3-chloro-1-phenyl-1-propanol in 97% enantiomeric purity which then was used as the starting material for the preparation of the corresponding enantiomers of S-tomoxetine and S-fluoxetine. Shortly thereafter, Gao & Sharpless, *J. Org. Chem*, 53, 4081, 1988, developed an enantioselective synthesis of both enantiomers of tomoxetine and of fluoxetine from cinnamyl alcohol via catalytic asymmetric epoxidation and regioselective reduction of the corresponding epoxycinnamyl alcohols. E. J. Corey and G. A. Reichard, *Tetrahedron Letters*, 30, No. 39, 5207 (1989) outlined a 4-step synthesis of enantiomerically pure fluoxetine from 3-chloropropiophenone in 77–82% overall yield with the key step being the enantioselective catalytic reduction of the ketone to 3-chloro-1-phenyl-1-propanol (CPP) in 99% yield and with 94% enantiomeric selectivity. Recrystallization afforded material of 100% enantiomeric purity with 82% recovery. These authors have recognized that compounds such as CPP are extremely useful in syntheses. The patentees in U.S. Pat. No. 5,104,899 recognized that the S(+)isomer of fluoxetine was the more desirable enantiomer, since it was found not to have certain side effects of the racemate such as nervousness, anxiety, insomnia, and adverse psychological effects. The patentees also recognize that the S-enantiomer had a faster onset of action with a quicker response rate.

The foregoing are examples of enantioselective synthesis. Enantioselective synthesis depends on chiral reagents of high enantiomeric purity which often are quite expensive. Consequently, another general approach is based on the efficient resolution of a precursor early in the synthesis of a chiral material. Resolution is effected with high enantiomeric purity and is followed by subsequent conventional synthetic techniques which maintain high enantiomeric purity in intermediates through final product formation. This approach is exemplified by the work of Schneider and Goergens, *Tetrahedron: Asymmetry*, No. 4, 525, 1992. These authors effected enzymatic resolution of CPP via enzymatic hydrolysis of the racemic acetate in the presence of a lipase from *Pseudomonas fluorescens* under close pH control with a phosphate buffer. The hydrolysis was halted after about 50% conversion to afford the R-alcohol while leaving unchanged the S-acetate, which subsequently could be hydrolyzed with base to the S-alcohol. From the enantiomerically pure alcohols the enantiomerically pure tomoxetine, fluoxetine, and nisoxetine could be prepared.

The Schneider and Goergens approach highlights a characteristic of methods based on resolution of a racemate which requires our attention. The authors used both the R- and S-CPP to prepare both R- and S-fluoxetine in high optical purity, although one enantiomer is substantially more desirable than the other (see U.S. Pat. No. 5,104,899, supra). Consequently, in practice only the more desirable enantiomer will be utilized in subsequent synthesis. There then results the economic burden of discarding the less desirable (or even undesirable) enantiomer—which is half of the raw material or (even worse) an intermediate in the synthesis of the desired enantiomer. Thus, it is imperative to somehow utilize the undesired enantiomer. Stated concisely, incident to a method of preparing medicinals of high optical purity based on using a raw material or intermediate of high enantiomeric purity obtained via resolution of its racemate is the requirement of utilizing the unwanted enantiomer produced as a byproduct in the resolution stage. Perhaps the most desirable utilization of the unwanted enantiomer would be to racemize it and recycle the racemate to the appropriate stage in the synthetic scheme; this application is directed precisely to such a process flow.

SUMMARY OF THE INVENTION

The purpose of the present invention is to present a process flow for preparation of the pharmaceutically more desirable (S)-enantiomer of various oxetines. An embodiment comprises reduction of a 3-substituted propiophenone to racemic 3-substituted-1-phenyl-1-propanol, resolution of the racemic propanol by simulated moving bed chromatography using a chiral adsorbent to afford at least one substantially pure enantiomer of the propanol, utilization of the substantially pure enantiomer in the synthesis of the pharmaceutically more desirable (S) enantiomer of an oxetine, racemization of the propanol enantiomer not further used in oxetine synthesis with its recycle to the resolution stage. In a specific embodiment (S)-3-X-1-phenyl-1-propanol is utilized as the substantially pure enantiomer. In another embodiment the racemization of the undesirable enantiomer of the propanol is effected by oxidation to propiophenone with its subsequent reduction to the racemic propanol.

A different embodiment comprises the conversion of cinnamyl derivatives, $C_6H_5CH=CHCH_2X$, to the racemic epoxide, resolution of the racemic epoxide by simulated moving bed chromatography using a chiral adsorbent to afford at least one substantially pure enantiomer of the epoxide, utilization of the substantially pure epoxide enantiomer in the synthesis of the (S)-oxetine, and racemization of the other epoxide enantiomer with recycle. Alternatively, the racemic epoxide may be regioselectively reduced to give the 3-X-1-phenyl-1-propanol with subsequent resolution as described in the foregoing section. Other embodiments will be apparent from the ensuing discussion.

DESCRIPTION OF THE INVENTION

Our invention is better understood in the context of some general synthetic route to racemic oxetines, a class of compounds having the formula

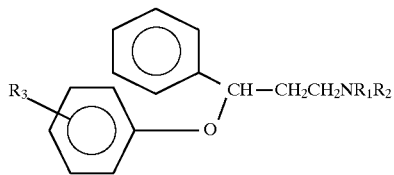

In a preferred embodiment, $R_1=H$, $R_2=CH_3$, and $R_3=4$-$CF_3$, 2-$CH_3$, or 2-$C_2H_5O$. The specific features of one generalized preparative route, depicting only those features of central interest here, are given in equation 1.

$$C_6H_5C(O)CH_2CH_2X \rightarrow C_6H_5CH(OH)CH_2CH_2X \rightarrow \rightarrow C_6H_5CH(OY)CH_2CH_2NHCH_3 \quad (1)$$

It is readily seen that in the preparation of racemic oxetines there are three key elements: reduction of the carbonyl group of a 3-substituted propiophenone to the corresponding benzylic alcohol; replacement of the 1-hydroxyl group with an —OY group; and conversion of X to $NHCH_3$. The preparative scheme we propose is represented by equation (2).

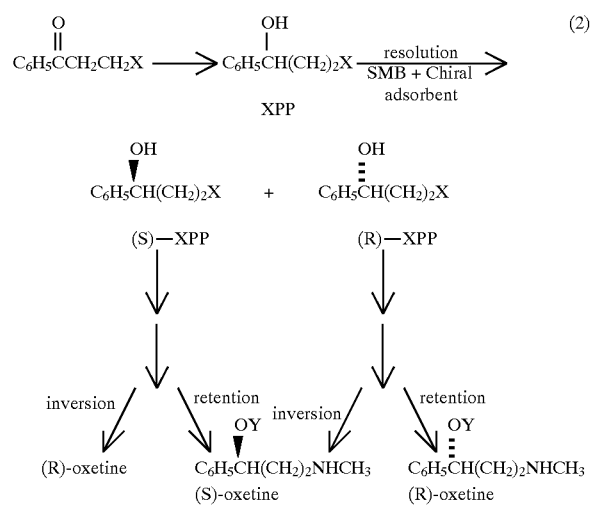

Note that the enantiomer of XPP desired to afford the (S)-oxetines depends upon whether there is inversion or retention of configuration in converting the hydroxyl group on carbon 1 to a OY group. An advantage of our invention is that the conditions of resolution of racemic XPP may be readily optimized for production of either substantially pure (R)-XPP or substantially pure (S)-XPP. Consequently the same resolution process may be used regardless of which particular synthetic scheme based on 3-XPP is employed. The process flow for the case of inversion of configuration is shown in scheme A of FIG. 1, whereas that for the case of retention of configuration is shown in scheme B.

Another generalized synthetic route to oxetines is based on the epoxidation of cinnamyl alcohol. Since equivalent results may be obtained with groups other than hydroxyl on the cinnamyl residue, we represent raw material as $C_6H_5CH=CHCH_2X$, and the synthesis is summarized in equation (3).

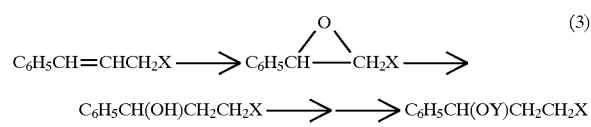

The preparative scheme we propose is represented by equation (4).

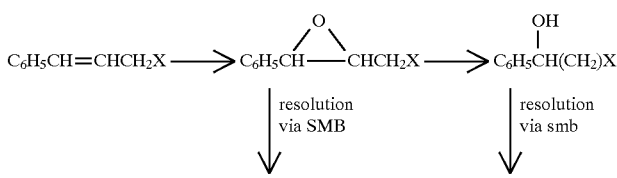

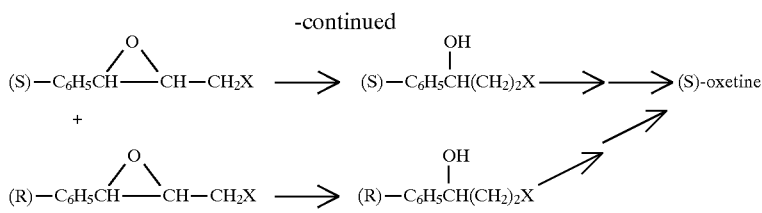
-continued

Figure 2A:
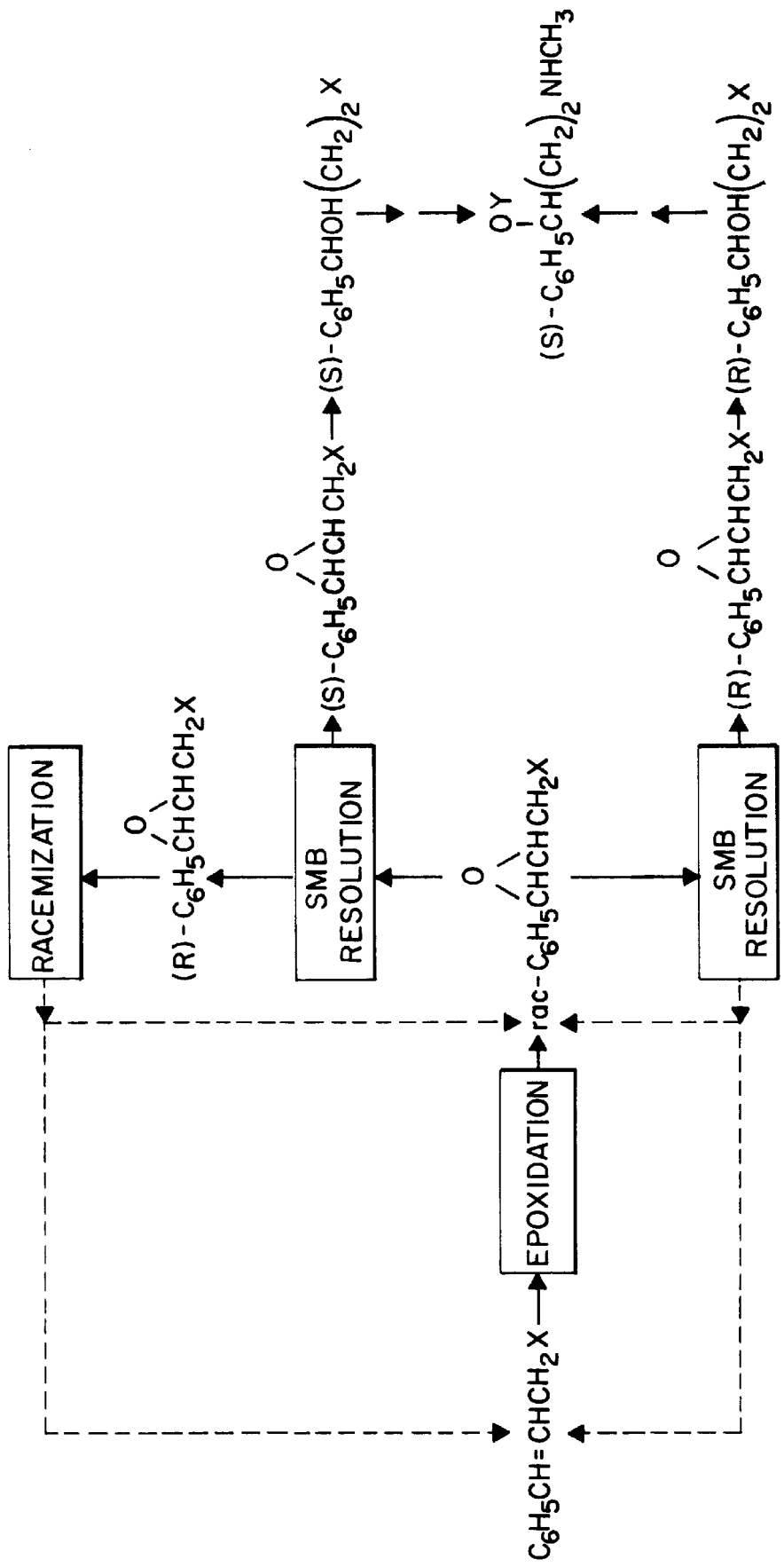
Figure 2B:
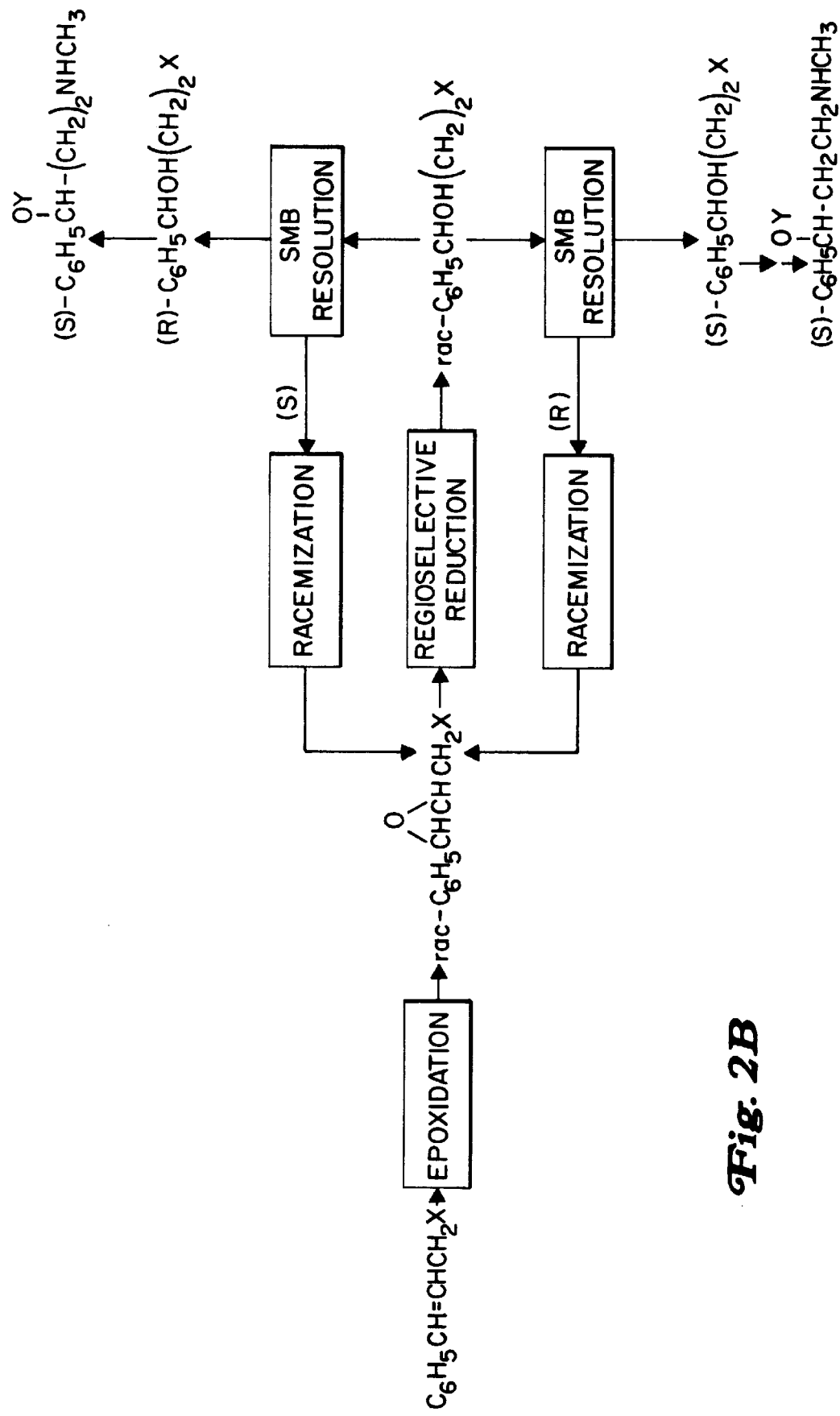

The process flow for this branch of our invention is shown in FIG. 2, where the case of inversion of configuration at the benzylic carbon is scheme A, and retention is given as scheme B.

In either case the central feature is the use of simulated moving bed chromatography using a chiral adsorbent to afford a substantially pure enantiomer subsequently employed in the preparation of an (S)-oxetine with racemization of the undesired enantiomer and its subsequent recycle to the resolution stage. Since simulated moving bed chromatography is a continuous process, quality control can be more effective and itself can be continuous in the context that separation parameters may be changed incrementally at frequent intervals.

Figure 1:
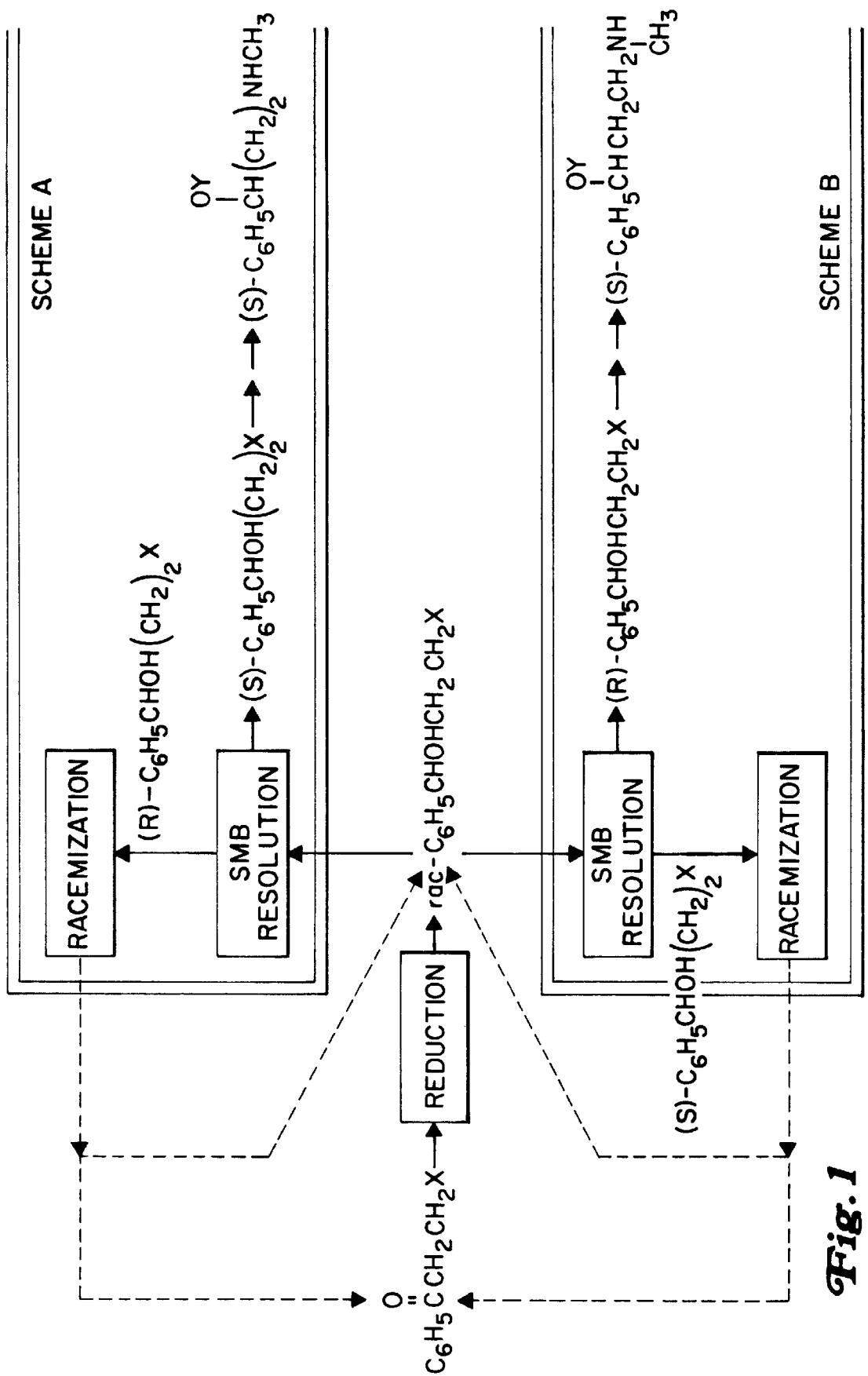
FIGS. 1 and 2(a and b) represent process flows for the preparation of (S)-oxetines utilizing simulated moving bed chromatography to resolve an intermediate relatively early in the synthetic preparative route.

Before describing the specifics of the processes in FIGS. 1 and 2 we will here briefly review simulated moving bed chromatography. The advantages of the moving bed of adsorbent in a countercurrent separation process has been long recognized. Because of the difficulty of an actual moving adsorbent bed, a flow scheme has been devised which maintains the process features of continuous countercurrent flow of fluid and solid without the actual movement of solids—i.e., a simulated moving bed.

In simulated moving bed processes the adsorption and desorption operations are continuously occurring which allows both continuous production of an extract and a raffinate stream with the continual use of feed and desorbent streams. A preferred embodiment of this process utilizes what is known in the art as the simulated moving bed countercurrent flow system. The operating principals and sequence of such a flow system are described in U.S. Pat. No. 2,985,589.

Simulated moving bed chromatography is a flow scheme which has been devised which maintains the process features of continuous countercurrent flow of fluid and solid without actual movement of the solid. The simulated moving bed technique has been described in R. A. Meyers, *Handbook of Petroleum Refining Processes*, pages 8–85 to 8–87, McGraw-Hill Book Company (1986). The technique has been applied commercially to a number of processes such as a separation of p-xylene from C8 aromatic isomers, the separation of linear paraffins from branched-chain and cyclic hydrocarbons, and a process to separate fructose and glucose from mixtures thereof, to name just a few.

Simulated moving bed chromatography may be readily applied to resolution of racemates simply by using a chiral adsorbent. See, e.g., M. Negawa and F. Shoji, *J. Chrom.*, 590, (1992), 113–7; M. J. Gattuso, B. McCullough, and J. W. Priegnitz presented at Chiral Europe '94 Symposium, Spring Innovations, Nice, France, Sep. 19–20, 1944.

A necessary feature of our invention is the adjustment of separation conditions to optimize the production of the desired enantiomer of high enantiomeric purity, i.e., optimize the formation of substantially pure desired enantiomer. By "substantially pure" is meant material of at least 95% enantiomeric purity, preferably at least 97% enantiomeric purity.

Another necessary feature is the racemization of the undesired enantiomer obtained by SMB resolution of the racemate. Any racemization means proceeding at high yield and with good selectivity will suffice. Satisfaction of these requirements maximizes the utilization of racemic starting material while minimizing the overall process cost. Referring to FIG. 2, the undesired enantiomer of XPP may be racemized by oxidation of the hydroxyl groups to a carbonyl group, thereby affording the propiophenone, which is the basic raw material in the synthetic route portrayed. Racemization of the alcohol also may be effected in acidic or basic media by means well known in the art. We emphasize again that any racemization means will suffice; what is necessary is that the racemate be obtained in good yield, with high selectivity, and at a minimum cost. In the process depicted in FIG. 2 racemization can be effected either of the benzylic alcohol, by means discussed above, or of the precursor epoxide by conversion of the epoxide to olefin using a reagent such as triphenylphosphine.

What is claimed is:

1. In a process for preparation of compounds I of formula

by converting a propiophenone II of formula

under achiral conditions to the racemic alcohol III of formula

and selectively converting racemic alcohol III to racemic compounds I, where $R_1$ is hydrogen or a lower alkyl containing from 1 up to about 5 carbon atoms, $R_2$ is a lower alkyl containing from 1 up to about 5 carbon atoms, where Ar is 4-trifluoromethylphenyl, 2-methylphenyl, or 2-ethoxyphenyl, and where X is a halogen, hydroxyl, ester, or amino group, the improvement comprising the selective preparation of (S)-I of at least 95% enantiomeric purity by:
  a. resolving racemic alcohol III by simulated moving bed chromatography using a chiral adsorbent to afford a first enantiomer of III in at least 95% enantiomeric purity and a second enantiomer of III; and
  b. selectively converting the first enantiomer of alcohol III to compounds I having the (S) configuration with at least 95% enantiomeric purity.

2. The process of claim 1 where $R_1$ is hydrogen.
3. The process of claim 1 where X is chlorine.
4. The process of claim 1 where $R_2$ is methyl.
5. The process of claim 1 where $R_1$ is hydrogen and $R_2$ is methyl.
6. The process of claim 1 where the first enantiomer of III is of at least 97% enantiomeric purity.
7. The process of claim 1 further characterized in that the second enantiomer of III is racemized to the racemic alcohol and recycling said racemic alcohol to stage (a).

8. The process of claim 7 where $R_1$ is hydrogen.
9. The process of claim 1 where X is chlorine.
10. The process of claim 1 where $R_2$ is methyl.
11. The process of claim 1 where $R_1$ is hydrogen and $R_2$ is methyl.
12. In a process for preparation of compounds I of formula

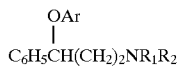

by converting a 3-substituted-1-phenylpropene of formula IV

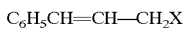

under achiral conditions to the racemic epoxide V of formula

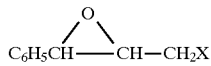

and selectively converting racemic epoxide V to racemic compounds I, where $R_1$ is hydrogen or a lower alkyl containing from 1 up to about 5 carbon atoms, $R_2$ is a lower alkyl containing from 1 up to about 5 carbon atoms, where Ar is 4-trifluoromethylphenyl, 2-methylphenyl, or 2-ethoxyphenyl, and where X is a halogen, hydroxyl, ester, or amino group, the improvement comprising the selective preparation of (S)-I of at least 95% enantiomeric purity by:
  a. resolving racemic epoxide V by simulated moving bed chromatography using a chiral adsorbent to afford a first enantiomer of V in at least 95% enantiomeric purity and a second enantiomer of V; and
  b. selectively converting the first enantiomer of epoxide V to compounds I having the (S) configuration with at least 95% enantiomeric purity.
13. The process of claim 12 where $R_1$ is hydrogen.
14. The process of claim 12 where X is chlorine.
15. The process of claim 12 where $R_2$ is methyl.
16. The process of claim 12 where $R_1$ is hydrogen and $R_2$ is methyl.
17. The process of claim 12 where the first enantiomer of III is of at least 97% enantiomeric purity.
18. In a process for preparation of compounds I of formula

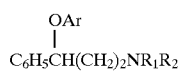

by converting a 3-substituted-1-phenylpropene of formula IV

under achiral conditions to the racemic epoxide V of formula

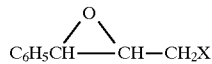

and selectively converting racemic epoxide V to racemic compounds I via the racemic alcohols III, where $R_1$ is hydrogen or a lower alkyl containing from 1 up to about 5 carbon atoms, $R_2$ is a lower alkyl containing from 1 up to about 5 carbon atoms, where Ar is 4-trifluoromethylphenyl, 2-methylphenyl, or 2-ethoxyphenyl, and where X is a halogen, hydroxyl, ester, or amino group, the improvement comprising the selective preparation of (S)-I of at least 95% enantiomeric purity by:
  a. resolving racemic alcohol III by simulated moving bed chromatography using a chiral adsorbent to afford a first enantiomer of III in at least 95% enantiomeric purity and a second enantiomer of III; and
  b. selectively converting the first enantiomer of alcohol III to compounds I having the (S) configuration with at least 95% enantiomeric purity.
19. The process of claim 18 where $R_1$ is hydrogen.
20. The process of claim 18 where X is chlorine.
21. The process of claim 18 where $R_2$ is methyl.
22. The process of claim 18 where $R_1$ is hydrogen and $R_2$ is methyl.
23. The process of claim 18 where the first enantiomer of III is of at least 97% enantiomeric purity.
24. The process of claim 18 further characterized in that the second enantiomer of III is racemized to the racemic alcohol and recycling said racemic alcohol to stage (a).

* * * * *